US00RE50551E

(19) United States
(12) Reissued Patent
Dokken et al.

(10) Patent Number: US RE50,551 E
(45) Date of Reissued Patent: Aug. 26, 2025

(54) TINTED ANTISEPTIC SOLUTIONS HAVING IMPROVED STABILITY

(71) Applicant: CAREFUSION 2200, INC., San Diego, CA (US)

(72) Inventors: Kenneth M. Dokken, El Paso, TX (US); Tenoch Benitez, El Paso, TX (US); James Bardwell, Downingtown, PA (US)

(73) Assignee: CareFusion 2200, Inc., San Diego, CA (US)

(21) Appl. No.: 16/676,791

(22) Filed: Nov. 7, 2019

Related U.S. Patent Documents

Reissue of:
(64) Patent No.: 9,821,066
Issued: Nov. 21, 2017
Appl. No.: 13/841,297
Filed: Mar. 15, 2013

(51) Int. Cl.

| | |
|---|---|
| ***A61K 47/32*** | (2006.01) |
| ***A61B 46/00*** | (2016.01) |
| ***A61K 9/00*** | (2006.01) |
| ***A61K 9/70*** | (2006.01) |
| ***A61K 31/155*** | (2006.01) |
| ***A61K 31/444*** | (2006.01) |
| ***A61L 26/00*** | (2006.01) |

(52) U.S. Cl.
CPC ..... *A61K 47/32* (2013.01); *A61B 46/40* (2016.02); *A61K 9/0014* (2013.01); *A61K 9/7015* (2013.01); *A61K 31/155* (2013.01); *A61K 31/444* (2013.01); *A61L 26/0014* (2013.01); *A61L 26/0066* (2013.01); *A61L 2300/404* (2013.01)

(58) Field of Classification Search
CPC ..... A61K 47/32; A61L 26/0066
See application file for complete search history.

(56) References Cited

U.S. PATENT DOCUMENTS

2003/0198673 A1* 10/2003 Oshlack et al. ..... A61K 9/5026 424/468
2004/0022755 A1* 2/2004 Kamath ..... A61K 9/2072 424/70.16
2004/0053201 A1* 3/2004 Dovgan ..... A61C 19/063 424/49
2009/0156406 A1* 6/2009 Dujardin et al. ..... A01N 25/10 514/772.3
2010/0022654 A1 1/2010 Asmus et al.
2010/0221193 A1 9/2010 Huang et al.
2011/0274770 A1 11/2011 Scholz et al. ..... A01N 59/12 424/672

FOREIGN PATENT DOCUMENTS

CA 1290250 * 10/1991
CA 1290250 C * 10/1991 ..... A01N 25/24
EP 2 196 225 A2 6/2010
EP 2499913 A1 9/2012
WO WO 2009/058144 A1 5/2009

OTHER PUBLICATIONS

International Search Report and Written Opinion corresponding to International Application No. PCT/US14/25484.

Extended European Search Report of related European Patent Application No. 14770089.2 dated Oct. 20, 2016.

* cited by examiner

*Primary Examiner* — Timothy J. Kugel

(74) *Attorney, Agent, or Firm* — ArentFox Schiff & Care Fusion

(57) ABSTRACT

An antiseptic solution including, a cationic antiseptic agent, a film forming polymer, an anionic tinting agent, and a solvent, wherein the cationic antiseptic agent, the film forming polymer and the anionic tinting agent each remain solubilized within the solution for greater than about 1 hour at 25° C. and 60% relative humidity. The antiseptic agent is preferably octenidine dihydrochloride or chlorhexadine gluconate. The film forming polymer is preferably an acrylate polymer. The solvent is preferably ethanol, isopropanol, and n-propanol. When a drape is adhered to a dried surgical film via the antiseptic solution, the force required to peel the drape from the surgical film is at least about 105 g/25 mm.

27 Claims, No Drawings

TINTED ANTISEPTIC SOLUTIONS HAVING IMPROVED STABILITY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The invention relates to antiseptic solutions, and more particularly, to antiseptic solutions comprising film forming polymers, antiseptic agents, and tinting agents.

BACKGROUND OF THE INVENTION

Solutions containing antiseptics may be applied to a patient's skin to kill bacteria prior to performing a medical procedure. The solutions may also be used to improve the adhesion of a drape to the patient's skin. Solutions with higher tackiness provide greater adhesion of a drape to the skin. Known antiseptic solutions are sometimes tinted so that the solution is visible when applied to the skin. However, in existing antiseptic solutions when a tinting agent is present, the solution becomes unstable. That is, components of the solution precipitate out over a relatively short amount of time, for example within twenty minutes to hour after the solution is prepared. Furthermore, the adhesion property of the solution can be reduced or lost entirely when the tint is added.

One approach for avoiding this problem is to mix the tint into the antiseptic solution just before application to the skin. However, this requires extra work for the practitioner and the solution can still become unstable (i.e., one or more of the components of the solution will precipitate out) quickly after the tint is added. Additionally, from a manufacturing/supply perspective, it is desirable for an antiseptic solution having tint to remain stable for as long as possible, thereby having a longer shelf life.

U.S. Pat. No. 4,374,126 to Cardarelli et al. is directed to a composition for a film forming antimicrobial material comprising alcohol carboxylated polycrylate.

U.S. Pat. No. 5,763,412 to Khan et al. is directed to an antimicrobial film forming composition including a film forming material and an antimicrobial agent, specifically containing chlorhexidine gluconate.

U.S. Patent Application Publication No. 2008/0108674 to Magallon et al. is directed to antiseptic solutions and compatible dyes, specifically anionic dyes.

U.S. Patent Application Publication No. 2008/0103526 to Vogt et al. is directed to a surgical suture material with antimicrobial surface containing a) at least one fatty acid, b) octenidine dichloride and/or dequalinium chloride and c) optionally oligomeric lactic acid esters.

U.S. Patent Application Publication No. 2007/0231051 to Flores et al. is directed to antiseptic solution in amount sufficient to be applied to a desired surface and to have an antimicrobial effect on the desired surface, the antiseptic solution comprising aqueous chlorhexidine gluconate; and at least one porous element, wherein the at least one porous element selectively removes undesired by-products from the antiseptic solution when the antiseptic solution contacts the at least one porous element.

U.S. Patent Application Publication No. 2007/0140990 to Fetissova et al. is directed to compositions that comprise a propolis extract; an oral care active compound chosen from: a cationic antibacterial agent, an anti-attachment agent, a biofilm disruption agent, and an anti-inflammatory agent; and a source of fluoride ions. In certain embodiments, the composition comprises an anionic polymeric linear polycarboxylate.

U.S. Patent Application Publication No. 2007/0014740 to Miller et al. is directed to a composition comprising (a) a cationic active ingredient; (b) a cationic-compatible inorganic particulate having a surface that is substantially inert to the cationic active ingredient; and (c) a cationic-compatible surfactant system.

U.S. Patent Application Publication No. 2006/0263323 to Hoang et al. is directed to an alcohol based hand surgical scrub, which includes cationic anti-microbial agent preservatives, cationic polymer film-forming agents and a skin emollient, and provides a long term residual, anti-microbial "invisible glove" on the skin.

U.S. Patent Application Publication No. 2005/0025794 to Wang et al. is directed to film-forming compositions including an optional active agent, water, a surfactant, and a water-soluble or water-dispersible vinyl polymer comprising amine group-containing side-chains and a copolymerized hydrophobic monomer; wherein the amine equivalent weight of the polymer is at least about 300 grams polymer per equivalent of amine group.

U.S. Patent Application Publication No. 2006/0194415 to Wang et al. is directed to film-forming compositions including an optional active agent, water, a surfactant, and a water-soluble or water-dispersible vinyl polymer comprising amine group-containing side-chains and a copolymerized hydrophobic monomer; wherein the amine equivalent weight of the polymer is at least about 300 grams polymer per equivalent of amine group.

Thus, there is a need for antiseptic solutions having tinting agents with improved stability as compared to known antiseptic solutions, while retaining sufficient adhesion properties.

Each of the above-listed references is hereby incorporated by reference in their entirety.

SUMMARY OF THE INVENTION

The invention relates to an antiseptic solution comprising, a cationic antiseptic agent, a film forming polymer, an anionic tinting agent, and a solvent, wherein the cationic antiseptic agent, film forming polymer and anionic tinting agent each remain solubilized for about 1 hour or more at 25° C. and 60% relative humidity.

In another aspect of the present invention, the cationic antiseptic agent, film forming polymer and anionic tinting agent each remain solubilized for about 24 hours or more at 25° C. and 60% relative humidity.

In another aspect of the present invention, the cationic antiseptic agent, film forming polymer and anionic tinting agent each remain solubilized for about 1 month or more at 25° C. and 60% relative humidity.

In another aspect of the present invention, the cationic antiseptic agent, film forming polymer and anionic tinting agent each remain solubilized for about 3 months or more at 25° C. and 60% relative humidity.

DETAILED DESCRIPTION OF THE INVENTION

The invention relates to an antiseptic solution having a film forming polymer, an antiseptic agent, and a tinting agent. The tinting agent is alternatively referred herein as "dye" or "tint." As used herein, the term "about" means within ±10%, preferably ±5%, more preferably ±1% of the given value. As used herein, the term "stable" with respect to a solution means that there is no discernible precipitation, particulates, haziness, or cloudiness present in the solution, when viewed by the unaided human eye (i.e., that all of the components in the solution remain solubilized). As used herein, the term "unstable" with respect to a solution means that there is a discernible precipitation, particulates, haziness, and cloudiness present in the solution, when viewed by the unaided human eye (i.e., at least one of the components of the solution has become at least partially unsolubilized). In other words, a "stable" solution appears clear to the naked eye while an unstable solution has at least some visible precipitation, particulate, haziness, or cloudiness.

It has been surprisingly found that a solution comprising combinations of cationic antiseptic agents, film forming polymers, and anionic tinting agents/dyes demonstrates enhanced stability as compared to an antiseptic solution without film forming polymer. That is, it has been surprisingly found that in an antiseptic solution having the above-stated combination of components, the solution components surprisingly remain solubilized at 25° C. and 60% relative humidity for a period of time longer than the period of time that the components remains solubilized at 25° C. and 60% relative humidity in known antiseptic solutions.

In an aspect of the present invention the antiseptic agent may comprise a cationic molecule (i.e, a molecule having a positive charge). More preferably, the antiseptic agent may comprise a cationic surfactant or a cationic biguanide derivative (i.e, compounds derived from biguanide). More preferably the cationic antiseptic compound may be a bis-(dihydropyridinyl)-decane derivative (i.e., compounds derived from bis-(dihydropyridinyl)-decane). The bis-(dihydropyridinyl)-decane derivative preferably includes octenidine salts and the biguanide preferably includes chlorhexadine salts. Preferably the octenidine salt may be octenidine dihydrochloride. Preferably the chlorhexadine may be a solution of chlorhexadine gluconate. The concentration of antiseptic agent in the solution may be from about 0.0001% to about 2.0% w/v, preferably about 0.01% to about 1% w/v, more preferably about 0.1% to about 0.4% w/v. When octenidine dihydrochloride or an octenidine salt is selected, the concentration in the solution may be from about 0.0001 to about 0.4% w/v, more preferably about 0.1% to about 0.2% w/v. When chlorhexadine gluconate is selected, the concentration in the solution may be about 0.5% to about 2% w/v.

The antiseptic solution may include an alcoholic solvent. The alcoholic solvent may be selected from ethanol, propanol, and n-propanol, and combinations thereof. The antiseptic solution may include from about 50 to about 90% v/v, preferably from about 70 to about 80% v/v alcoholic solvent.

The film forming polymer may be selected from acrylate polymers, such as acrylamide polymers, octylacrylamide polymers, methacrylate polymers, carboxyacrylate polymers, and polymers having dimethylaminoethyl methacrylate, butyl methacrylate, and methyl methacrylate side groups. The concentration of polymer may be varied depending on the particular alcohol and antiseptic present in the solution. In one aspect of the present invention, the concentration of the film forming polymer may be from about 0.1% to about 5% w/v, preferably about 0.2% to about 3% w/v, more preferably about 0.5% to about 2.0% w/v, and still more preferably about 0.75% to about 2.5% w/v.

Example acrylate polymers include DERMACRYL® AQF (2-propenoic acid, 2-methyl-, polymer with butyl 2-propenoate and methyl 2-methyl-2-propenoate), DERMACRYL® 79P (2-propenoic acid, 2-methyl-, 2-methylpropyl ester, polymer with 2-propenoic acid and N-(1,1,3,3tetramethylbutyl)-2-propenamide), each manufactured by Akzo Nobel Coatings Inc, and EUDRAGIT® E PO (poly (butyl methacylate-co-(2-dimethylaminoethyl) methacrylate-co-methyl methacrylate) manufactured by Evonik Industries. DERMACRYL® 79P is a hydrophobic, high molecular weight carboxylated acrylic copolymer. EUDRAGIT® E PO is a cationic copolymer based on dimethylaminoethyl methacrylate, butyl methacrylate, and methyl methacrylate In an aspect of the present invention the tinting agents/dyes are anionic. The concentration of dye present in the antiseptic solution may be about 0.01% to about 0.15% w/v, more preferably about 0.03% to about 0.12% w/v, and still more preferably about 0.05% to about 0.09% w/v.

The anionic dye may be any dye suitable for medical use, such as dyes approved by the Food and Drug Administration for use in food, drugs, and/or cosmetics (i.e., "D&C" or "FD&C" dyes). For example, the anionic dye may be selected from the group consisting of, but are not limited to, FD&C Blue No. 1 (Brilliant Blue FCF), FD&C Blue No. 2 (Indigo Carmine), FD&C Green No. 3 (Fast Green FCF), FD&C Red No. 3(Erythrosine), FD&C Red No. 40 (Altura Red), FD&C Yellow No. 5 (Tartrazine), FD&C Yellow No. 6 (Sunset Yellow FCF), D&C Yellow No. 8 (Fluorescein), D&C Orange No. 4, and combinations thereof. Combinations may be implemented to arrive at a particular color. For example, an orange tint may comprise both FD&C Red No. 40 and D&C Yellow No. 8.

In another aspect of the present invention, the antiseptic solution may include one or more plasticizers. The plasticizer may be an ester of an organic acid, for example, triethyl citrate and dibutyl sebacate. The concentration of plasticizer present in the antiseptic solution may be about 0.05% to about 2% w/v, more preferably about 0.75% to about 1.5%, and still more preferably about 0.1% to about 1% w/v Aspects of the present invention include a method of disinfecting a surface comprising applying the above-disclosed antiseptic solution to the surface. The surface may be human skin.

Other aspects of the present invention include a method of adhering a drape to a surface. The method includes applying the above-disclosed antiseptic solution to the surface. Then, the antiseptic solution is allowed to dry. Drying the antiseptic solution produces in a tacky film. After the tacky film has been formed, the drape is then contacted with the tacky film. The drape also contacts portions of the surface that do not have the tacky film formed thereon. Upon contacting the tacky film, the drape is adhered to the surface via the tacky film. In an aspect of the present invention, the force required to peel the drape from the surface is about 105 g/25 mm or more, preferably about 115 g/25 mm or more, more preferably about 120 g/25 mm or more. The surface may be human skin.

Aspects of the present invention further include an antiseptic applicator comprising the above-disclosed antiseptic solution contained therein.

EXAMPLES

Stability testing was performed on several example formulations of antiseptic solutions, according to the following procedures. Upon completion of a formulation, each formulation was initially assessed for precipitation, particulates, haziness, and cloudiness by the human eye unaided. The presence of any of these conditions was considered to be an unstable formulation. The initial state of the formulation was recorded as unstable or stable. Those samples that were initially stable were exposed to 25° C. and 60% relative humidity and then inspected at various times. The initial inspection was performed every hour. If the solution remained stable after a 24 hour period, then the solution was then inspected daily for one week. After one week, the samples were inspected every two days for a period of 30 days. After 30 days the samples were monitored on a weekly basis. At the first sign of any discernible precipitation, particulates, haziness, or cloudiness the samples were noted as unstable and the time in units of hours, days, or months, or years was recorded. Some samples were also tested at 5° C. and −20° C. to test stability of possible storage conditions. For the −20° C. testing, the samples often displayed cloudiness or haziness due to the low solubility of the polymer at these temperatures. However, because the conditions in which the solutions are actually used are much warmer (i.e., room temperature), the procedure for inspecting these formulations included an additional step of removing the sample from the −20° C. conditions and allowing it to reach room temperature before performing the inspection. If upon returning to room temperature, the precipitation, particulates, haziness, and cloudiness was not observed, the sample was considered stable and placed back into −20° C. conditions until the next inspection was performed. The samples that continued to display precipitation, particulates, haziness, and cloudiness after reaching room temperature were considered unstable.

The stability times for each of the example are compiled in Table I following the listing of examples. "Unstable" as used in Table 1 means that the initial solution was found to have discernible precipitation, particulates, haziness, or cloudiness before timing began (i.e., the solution was unstable at time zero).

Example 1

2.0% w/v Chlorhexidine Gluconate, 70% v/v Isoropyl Alcohol, 30% v/v deionized Water, 0.08% w/v FD&C Yellow 6. Example 1 does not contain polymer.

Example 2

2.0% w/v Chlorhexidine Gluconate, 70% v/v Isoropyl Alcohol, 1.75% v/w DERMACRYL® AQF, 30% v/v deionized Water. Example 2 does not contain tint.

Example 3

2.0% w/v Chlorhexidine Gluconate, 70% v/v Isopropyl Alcohol, 1.75% v/w DERMACRYL® AQF, 30% v/v deionized water, 0.08% w/v FD&C Yellow 6.

Example 4

0.2% w/v Octenidine dihydrochloride, 70% v/v isopropyl alcohol, 0.07% w/v D&C Orange 4, 25% v/v deionized water. Example 3 does not contain polymer Example 5

0.2% w/v Octenidine dihydrochloride, 75% v/v isopropyl alcohol, 1.75% w/v DERMACRYL® 79P, 25% v/v deionized water. Example 5 does not contain tint.

Example 6

0.2% w/v Octenidine dihydrochloride, 80% v/v isopropyl alcohol, 2.00% w/v DERMACRYL® 79P, 20% v/v deionized water. Example 6 does not contain tint.

Example 7

0.2% w/v Octenidine dihydrochloride, 75% v/v isopropyl alcohol, 1.75% w/v DERMACRYL® 79P, 25% v/v deionized water, 0.07% w/v D&C Orange 4

Example 8

0.2% w/v Octenidine dihydrochloride, 70% v/v isopropyl alcohol, 0.07% w/v D&C Orange 4, 25% v/v deionized water. Example 8 does not contain polymer.

Example 9

0.2% w/v Octenidine dihydrochloride, 75% v/v isopropyl alcohol, 1.75% w/v DEMACRYL® AQF, 25% v/v deionized water. Example 9 does not contain tint.

Example 10

0.2% w/v Octenidine dihydrochloride, 75% v/v isopropyl alcohol, 1.75% w/v DEMACRYL® AQF, 25% v/v deionized water, 0.07% w/v D&C Orange 4.

Example 11

0.1% w/v Octenidine dihydrochloride, 70% v/v isopropyl alcohol, 0.09% w/v mixture of 65% D&C Yellow No. 8 and 35% FD&C Red No. 40, 30% v/v deionized water. Example 11 does not contain polymer.

Example 12

0.1% w/v Octenidine dihydrochloride, 70% v/v isopropyl alcohol, 0.11% w/v mixture of 60% D&C Yellow No. 8 and 40% FD&C Red No. 40, 30% v/v deionized water. Example 12 does not contain polymer.

Example 13

0.1% w/v Octenidine dihydrochloride, 70% v/v isopropyl alcohol, 0.11% w/v mixture of 55% D&C Yellow No. 8 and 45% FD&C Red No. 40, 30% v/v deionized water. Example 13 does not contain polymer.

Example 14

0.1% w/v Octenidine dihydrochloride, 70% v/v isopropyl alcohol, 0.11% w/v mixture of 50% D&C Yellow No. 8 and 40% FD&C Red No. 40, 30% v/v deionized water. Example 14 does not contain polymer Example 15

0.1% w/v Octenidine dihydrochloride, 70% v/v isopropyl alcohol, 2.5% w/v EUDRAGIT® E PO, 1% w/v dibutyl sebacate, 30% v/v deionized water. Example 15 does not contain tint.

Example 16

0.1% w/v Octenidine dihydrochloride, 70% v/v isopropyl alcohol, 2.5% w/v EUDRAGIT® E PO, 1% w/v dibutyl sebacate, 0.09% w/v mixture of 65% D&C Yellow No. 8 and 35% FD&C Red No. 40, 30% v/v deionized water.

Example 17

0.1% w/v Octenidine dihydrochloride, 70% v/v isopropyl alcohol, 2.5% w/v EUDRAGIT® E PO, 1% w/v dibutyl sebacate, 0.11% w/v mixture of 60% D&C Yellow No. 8 and 40% FD&C Red No. 40, 30% v/v deionized water.

Example 18

0.1% w/v Octenidine dihydrochloride, 70% v/v isopropyl alcohol, 2.5% w/v EUDRAGIT® E PO, 1% w/v dibutyl sebacate, 0.11% w/v mixture of 55% D&C Yellow No. 8 and 45% FD&C Red No. 40, 30% v/v deionized water.

Example 19

0.1% w/v Octenidine dihydrochloride, 70% v/v isopropyl alcohol, 2.5% w/v EUDRAGIT® E PO, 1% w/v dibutyl sebacate, 0.11% w/v mixture of 50% D&C Yellow No. 8 and 50% FD&C Red No. 40, 30% v/v deionized water.

Example 20

0.1% w/v Octenidine dihydrochloride, 70% v/v isopropyl alcohol, 0.09% w/v mixture of 65% D&C Yellow No. 8 and 35% FD&C Red No. 40. Example 20 does not contain polymer, 30% v/v deionized water.

Example 21

0.1% w/v Octenidine dihydrochloride, 70% v/v isopropyl alcohol, 2.5% w/v EUDRAGIT® E PO, 1% w/v dibutyl sebacate, 0.4% w/v triethyl citrate, 30% v/v deionized water. Example 21 does not contain tint.

Example 22

0.1% w/v Octenidine dihydrochloride, 70% v/v isopropyl alcohol, 2.5% w/v EUDRAGIT® E PO, 1% w/v dibutyl sebacate, 0.4% w/v triethyl citrate, 0.11% w/v mixture of 65% D&C Yellow No. 8 and 35% FD&C Red No. 40, 30% v/v deionized water.

Example 23

2.0% w/v Chlorhexidine gluconate, 70% v/v Isopropyl Alcohol, 30% v/v Deionized Water. Example 23 does not contain polymer or tint.

Example 24

0.1% w/v Octenidine dihydrochloride, 70% v/v Isopropyl Alcohol, 2.5% w/v EUDRAGIT® EP O, 1% w/v Dibutyl sebacate, 0.4% w/v Triethyl citrate, 0.13% w/v mixture of 55% D&C Yellow No. 8/45% FD&C Red No. 40, 30% v/v deionized water.

Example 25

0.1% w/v Octenidine dihydrochloride, 70% v/v Isopropyl Alcohol, 2.5% w/v EUDRAGIT® EP O, 1% w/v Dibutyl sebacate, 0.4% w/v Triethyl citrate, 0.13% w/v mixture of 50% D&C Yellow No. 8/45% FD&C Red No. 40, 50% v/v deionized water.

Example 26

0.1% w/v Octenidine dihydrochloride, 70% v/v Isopropyl Alcohol, 2.5% w/v EUDRAGIT® EP O, 1% w/v Dibutyl sebacate, 0.4% w/v Triethyl citrate, 0.11% w/v mixture of 55% D&C Yellow No. 8/45% FD&C Red No. 40, 30% v/v deionized water.

Example 27

0.2% w/v Octenidine dihydrochloride, 70% v/v Isopropyl Alcohol, 1.75% w/v DERMACRYL® 79P, 0.07% w/v D&C orange 4, 25% v/v deionized water.

Example 28

0.2% w/v Octenidine dihydrochloride, 70% v/v Isopropyl Alcohol, 2.5% w/v DERMACRYL® 79P, 0.07% w/v D&C orange 4, 25% v/v deionized water.

Example 29

0.2% w/v Octenidine dihydrochloride, 70% v/v Isopropyl Alcohol, 1.75% w/v DEMACRYL® AQF, 0.07% w/v D&C orange 4, 30% v/v deionized water.

Example 30

0.2% w/v Octenidine dihydrochloride, 70% v/v Isopropyl Alcohol, 2.5% w/v DEMACRYL® AQF, 0.07% w/v D&C orange 4, 30% v/v deionized water.

Example 31

2.0% w/v Chlorhexidine gluconate, 75% v/v Isopropyl Alcohol, 1.75% w/v DEMACRYL® AQF, 0.08% w/v FD&C yellow 6, 25% v/v deionized water.

Example 32

2.0% w/v Chlorhexidine gluconate, 80% v/v Isopropyl Alcohol, 1.75% w/v DEMACRYL® AQF, 0.08% w/v FD&C yellow 6, 20% v/v deionized water.

TABLE 1

| Example | Stability at 25° C. | Stability at 5° C. | Stability at −20° C. |
|---|---|---|---|
| 1 | 2-4 hours | Unstable | Unstable |
| 2 | 1 year | 30 days | 2 days |
| 3 | 2 weeks | Unstable | Unstable |
| 4 | 3 days | Unstable | Unstable |
| 5 | 1 year 1 month | 30 days | 2 days |
| 6 | 1 year | 37 days | 2 days |
| 7 | 1 year 1 month | 33 days | 2 days |
| 8 | 5 days | Unstable | Unstable |
| 9 | 1 year | 30 days | 2 days |
| 10 | 6 months, 5 days | 32 days | 2 days |
| 11 | 12 days | Not tested | Not tested |
| 12 | 12 days | Not tested | Not tested |
| 13 | 12 days | Not tested | Not tested |
| 14 | 14 days | Not tested | Not tested |
| 15 | 30 days | Not tested | Not tested |
| 16 | 21 days | Not tested | Not tested |
| 17 | 20 days | Not tested | Not tested |
| 18 | 22 days | Not tested | Not tested |
| 19 | 34 days | Not tested | Not tested |
| 20 | 12 days | Not tested | Not tested |
| 21 | 15 days | Not tested | Not tested |
| 22 | 14 days | Not tested | Not tested |
| 23 | Not tested | Not tested | Not tested |
| 24 | Unstable | Not tested | Not tested |

TABLE 1-continued

| Example | Stability at 25° C. | Stability at 5° C. | Stability at −20° C. |
|---|---|---|---|
| 25 | Unstable | Not tested | Not tested |
| 26 | Unstable | Not tested | Not tested |
| 27 | Unstable | Not tested | Not tested |
| 28 | Unstable | Not tested | Not tested |
| 29 | Unstable | Not tested | Not tested |
| 30 | Unstable | Not tested | Not tested |
| 31 | Unstable | Not tested | Not tested |
| 32 | Unstable | Not tested | Not tested |

Examples 1-3 are comparable with each other, Examples 4-7 are comparable with each other, Examples 8-10 are comparable with each other, Examples 11-19 are comparable with each other, and Examples 20-22 are comparable with each other. Examples 1-3 show that when tint is added to an antiseptic solution, the stability significantly decreases (2-4 hours), however when the tint is added in combination with film forming polymer (DERMACRYL® AQF) the stability is increased (2-4 hours vs. 2 weeks). Examples 4-7 show a similar trend, that when tint is added in combination with film forming polymer (DERMACRYL® 79P), the stability is increased (3 days vs. 1 year). Examples 11-19 show a similar trend, that when tint is added in combination with film forming polymer (EUDRAGIT® E PO), the stability is increased (12-14 days vs. 21-34 days). Examples 21-22 show a similar trend, that when tint is added in combination with film forming polymer (EUDRAGIT® E PO), the stability is increased (12 days vs. 14 days).

The data also shows that particular relative amounts of the components contributed to the unexpected stability. As shown in Examples 24-32, formulations prepared with chlorhexidine gluconate were unstable at concentrations higher than 70% v/v isopropyl alcohol. Therefore, the higher isopropyl alcohol content can be unfavorable when other components such as dye are in the formulation. These formulations become hazy and form a clear viscous substance predominantly composed of polymer. When octenidine dihydrochloride is present, with concentrations higher than 2% w/v of polymer, the formulations become unstable showing various degrees of cloudiness and eventual precipitation of a white substance predominantly composed of polymer.

Thus, the above data demonstrates that an antiseptic solution comprising a combination of film forming polymer and tinting agent surprisingly has improved stability as compared to an antiseptic solution comprising tint, but no polymer.

Testing was also performed to determine the adhesion properties of the antiseptic solutions when used in combination with a drape. As noted above, while tint stability is desirable, it is also desirable for the antiseptic solution to remain adhesive to a drape.

The adhesive property was measured using two tests, an "irrigation stress test" and a "wet peel test." The irrigation stress test determines the visual bond quality of a surgical drape film and adhesive to a synthetic skin substrate after exposure to water and stress in a probe flex fixture. The probe flex fixture replicates movement in an orthopedic surgery procedure, as a challenging environment for drape adhesion due to movement, irrigation and length of time for this type of operation. A scale of 1 to 5 was used to quantify the results, with 1 being no edge lift of the drape from the substrate from initial application and 5 being total edge lift (i.e., 1 is most adhesive and 5 is least adhesive). Tests were performed by applying surgical solution onto the synthetic skin analog consisting of latex film and drying before testing. The drying condition was 73° F. and 50% relative humidity for four minutes. Application and testing was performed in a simulated hospital operating room environment, 65° F. and 40% relative humidity. The drape was applied on the top of the dried solution which had been applied on top of the latex. The latex-solution skin preparation-drape assembly was applied on to the test platform with double-sided tape. Four half inch incisions into the assembly were made using a razor blade. Four cylinder-shape probes were placed through the pre-cut incisions. Four 100 stroke cycles generated from the probe were performed with two minutes between each cycle. Water flows from under the test platform through the insertion points of the simulated surgical rods. The water passes over and around the latex-skin prep-drape layers as the surgical rods are in motion. This set-up allows water to diffuse into the interface between drape and latex film. This simulates how the fluid may weaken the drape adhesion if the surgical solution does not provide good water resistance.

The test method to measure wet peel strength was an adaptation of ASTM D 3330 part F, "Peel Adhesion of Pressure Sensitive Tapes". The Wet Peel test measures the force required to remove a drape from the test surface after the samples are exposed to 0.9% saline. During initial testing, latex film was laminated on foam backing material to simulate the texture deformability and wrinkling of human skin. Latex was later laminated to textured ABS plastic panels to have a more consistent texture. The surgical solution under test was applied on latex film, dried and exposed to 0.9% saline solution before the peel test. The drying and environment conditions were the same as the conditions for irrigation stress tests. The drape was applied on the dried surgical film. The assembly was immersed in 0.9% NaCl saline solution for one hour. 180° peel was conducted to study how much force is required to remove the drape from the latex film. The force was measured in grams (g)/25 mm.

In an aspect of the present invention, the amount of force required to peel the drape from the dried surgical film is about 105 g/25 mm or more, preferably about 115 g/25 mm or more, more preferably about 120 g/25 mm or more.

The results of the irrigation stress test are provided in Table 2 and the results of the wet peel test are provided in Table 3:

TABLE 2

| Irrigation Stress Test | | | | | | | |
|---|---|---|---|---|---|---|---|
| Example | Test 1 | Test 2 | Test 4 | Test 4 | Test 5 | Test 6 | Average |
| 23 | 3 | 4 | 5 | 4 | not tested | not tested | 4 |
| 9 | 0 | 0 | 0 | not tested | not tested | not tested | 0 |
| 6 | 0 | 0 | 0 | not tested | not tested | not tested | 0 |
| 3 | 3 | 1 | 2 | 3 | 4 | 2 | 2.5 |
| 2 | 1 | 2 | not tested | not tested | not tested | not tested | 1.5 |

Key:
0 - No change at all (most adhesive)
1 - No Edge Lift
2 - Minimal Edge Lift
3 - Moderate edge lift
4 - Significant edge lift
5 - Total edge lift (least adhesive)

TABLE 3

| Wet Peel Test | | | |
|---|---|---|---|
| Example | g/25 mm | σ | n |
| 23 | 104.3 | 22.1 | 5 |
| 9 | 318.8 | 40 | 5 |
| 6 | 344.7 | 40.2 | 5 |
| 3 | 122.9 | 47.7 | 6 |

σ = standard deviation
n = number of tests

Table 2 shows that formulations containing Octenidine dihydrochloride with DERMACRYL® AQF without tint (Example 9) and DERMACRYL® 79P without tint (Example 6) demonstrated superior adhesion (no change or edge lift) when compared to the other examples. The solution containing Chlorhexidine gluconate, DERMACRYL® AQF, and no tint (Example 3) displayed minimal to moderate edge lift compared to the solution with Chlorhexidine gluconate and no polymer or tint (Example 23) which displayed significant edge lift. In addition, the results show that the presence of tint in the formulation with polymer (Example 3) reduces adhesion as compared to a similar solution having polymer but not tint (Example 2).

The wet peel test results provided in Table 3 confirms the results of the irrigation stress test. The wet peel test confirmed that the Octenidine dihydrochloride with DERMACRYL® AQF (Example 9) and DERMACRYL® 79P (Example 6) demonstrated superior adhesion as the required force to remove the drape was 319 ad 345 g/25 mm, respectively. The solution with tint and DERMACRYL® AQF (Example 3) provided only slightly better adhesion than the solution without polymer or tint (Example 23).

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An antiseptic solution comprising:

about 0.0001% w/v to about 2.0% w/v of a cationic antiseptic agent, wherein the cationic antiseptic agent comprises a cationic surfactant and one selected from the group consisting of a biguanide or a bis-(dihydropyridinyl)-decane derivative;

about 0.1% w/v to about 5% w/v of a film forming polymer comprising an acrylate polymer;

about 0.01% to about 0.15% w/v of an anionic tinting agent; and a solvent, wherein the polymer is selected from the group consisting of 2-propenoic acid, 2-methyl-, polymer with butyl 2-propenoate and methyl 2-methyl-2-propenoate and 2-propenoic acid, 2-methyl-, 2-methylpropyl ester, polymer with 2-propenoic acid and N-(1,1,3,3tetramethylbutyl)-2-propenamide, and the cationic antiseptic agent, the film forming polymer, and the anionic tinting agent each remain solubilized within the solution for about 1 hour or more at 25° C. and 60% relative humidity.

2. The antiseptic solution of claim 1, wherein the cationic antiseptic agent, the film forming polymer, and the anionic tinting agent each remain solubilized for about 24 hours or more at 25° C. and 60% relative humidity.

3. The antiseptic solution of claim 1, wherein the cationic antiseptic agent, the film forming polymer, and the anionic tinting agent each remain solubilized for about 1 month or more at 25° C. and 60% relative humidity.

4. The antiseptic solution of claim 1, wherein the cationic antiseptic agent, the film forming polymer, and the anionic tinting agent each remain solubilized for at 3 month or more at 25° C. and 60% relative humidity.

5. The antiseptic solution of claim 1, wherein the antiseptic agent comprises an octenidine salt or chlorhexadine salt.

6. The antiseptic solution of claim 1, wherein the antiseptic agent comprises octenidine dihydrochloride or clorhexadine gluconate.

7. The antiseptic solution of claim 1, wherein the anionic tinting agent comprises an agent selected from the group consisting of Blue No. 1, Blue No. 2, Green No. 3, Red No. 3, Red No. 40, Yellow No. 5, Yellow No. 6, Yellow No. 8, Orange No. 4, and combinations thereof.

8. The antiseptic solution of claim 1, wherein the solvent comprises an alcoholic solvent.

9. The antiseptic solution of claim 8, wherein the solvent comprises an alcoholic solvent selected from the group consisting of ethanol, isopropanol, and n-propanol.

10. The antiseptic solution of claim 8, wherein the concentration of the solvent is about 50 to about 80% v/v.

11. The antiseptic solution of claim 1, further comprising a plasticizer.

12. The antiseptic solution of claim 11, wherein the plasticizer comprises triethyl citrate or dibutyl sebacate.

13. The antiseptic solution of claim 11, wherein the concentration of the plasticizer is about 0.05% to about 2% w/v.

14. A method of disinfecting a surface comprising applying the antiseptic solution of claim 1 to the surface.

15. The method of claim 14, wherein the surface is human skin.

16. A method of adhering a drape to a surface, the method comprising:

applying the antiseptic solution of claim 1 to the surface;

allowing the antiseptic solution to dry, thereby producing a tacky film; and contacting the drape with the tacky film such that the drape is adhered to the surface via the tacky film.

17. The method of claim 16, wherein the surface is human skin.

18. The method of claim 16, wherein the force required to peel the drape from the surface is about 105 g/25 mm or more.

19. An antiseptic applicator comprising the antiseptic solution of claim 1 contained therein.

*20. An antiseptic solution comprising:*

*about 0.0001% w/v to about 2.0% w/v of a cationic antiseptic agent, wherein the cationic antiseptic agent comprises a cationic surfactant and one selected from the group consisting of a biguanide or a bis-(dihydropyridinyl)-decane derivative;*

*about 70% v/v of an alcoholic solvent comprising isopropanol;*

*a film forming polymer selected from octylacrylamide polymers, carboxyacrylate polymers, and polymers having dimethylaminoethyl methacrylate, butyl methacrylate, or methyl methacrylate side groups; and*

*an anionic tinting agent,*

*wherein the cationic antiseptic agent, the film forming polymer, and the anionic tinting agent each remain solubilized within the antiseptic solution for about 1 month or more at 25° C. and 60% relative humidity, and*

*wherein when a drape is adhered to a dried surgical film via the antiseptic solution, the force required to peel the drape from the surgical film is about 105 g/25 mm or more.*

*21. The antiseptic solution of claim 20, wherein the concentration of the film forming polymer in the antiseptic solution is about 0.1% w/v to about 5% w/v.*

*22. The antiseptic solution of claim 20, wherein the cationic antiseptic agent, the film forming polymer, and the anionic tinting agent each remain solubilized within the antiseptic solution for about 3 months or more at 25° C. and 60% relative humidity.*

*23. The antiseptic solution of claim 20, wherein the anionic tinting agent comprises an agent selected from the group consisting of Blue No. 1, Blue No. 2, Green No. 3, Red No. 3, Red No. 4, Yellow No. 5, Yellow No. 6, Yellow No. 8, Orange No. 4, and combinations thereof.*

*24. The antiseptic solution of claim 20, wherein the antiseptic solution further comprises a plasticizer.*

*25. The antiseptic solution of claim 24, wherein the plasticizer comprises an ester of an organic acid.*

*26. The antiseptic solution of claim 24, wherein the concentration of the plasticizer in the antiseptic solution is about 0.05% to about 2% w/v.*

*27. The antiseptic solution of claim 20, wherein the concentration of the anionic tinting agent in the antiseptic solution is about 0.01% to about 0. 15% w/v.*

* * * * *